(12) United States Patent
Wang et al.

(10) Patent No.: US 12,139,701 B2
(45) Date of Patent: *Nov. 12, 2024

(54) BIOFUNCTIONAL MATERIALS

(71) Applicants: Toyota Motor Corporation, Toyota (JP); The University of Akron, Akron, OH (US)

(72) Inventors: Ping Wang, North Oaks, MN (US); Minjuan Zhang, Ann Arbor, MI (US); Hongfei Jia, Ann Arbor, MI (US); Archana H. Trivedi, Mumbai (IN); Masahiko Ishii, Okazaki (JP)

(73) Assignees: Toyota Motor Corporation, Toyota (JP); The University of Akron, Akron, OH (US)

( * ) Notice: Subject to any disclaimer, the term of this patent is extended or adjusted under 35 U.S.C. 154(b) by 845 days.

This patent is subject to a terminal disclaimer.

(21) Appl. No.: 16/255,416

(22) Filed: Jan. 23, 2019

(65) Prior Publication Data

US 2019/0153422 A1 May 23, 2019

Related U.S. Application Data

(63) Continuation of application No. 15/790,846, filed on Oct. 23, 2017, now Pat. No. 10,781,438, which is a
(Continued)

(51) Int. Cl.
*C12N 11/14* (2006.01)
*C09D 5/14* (2006.01)
(Continued)

(52) U.S. Cl.
CPC ............... *C12N 11/14* (2013.01); *C09D 5/14* (2013.01); *C09D 5/1637* (2013.01);
(Continued)

(58) Field of Classification Search
CPC ...... C09D 5/1637; C09D 5/14; C09D 5/1687; C12N 11/14; C12N 9/54; C12N 9/20;
(Continued)

(56) References Cited

U.S. PATENT DOCUMENTS 3,220,928 A 11/1965 Brenner
3,519,538 A 7/1970 Messing et al.
(Continued)

FOREIGN PATENT DOCUMENTS

AU 2003304222 A1 1/2005
AU 2004257205 A1 1/2005
(Continued)

OTHER PUBLICATIONS

Minier,et al. Covalent Immobilization of Lysozyme on Stainless Steel Interface Spectroscopic Characterization and Measurement of Enzymatic Activity Langmuir 2005, 21, 5957-5965 (Year: 2005).*
(Continued)

*Primary Examiner* — Angela C Brown-Pettigrew
*Assistant Examiner* — Preeti Kumar
(74) *Attorney, Agent, or Firm* — Dinsmore & Shohl LLP

(57) ABSTRACT

Provided are methods and compositions for self-cleaning that include a digestive protein capable of decomposing stain forming molecules, a substrate applied to a solid surface, and a linker moiety bound to an outer surface of said substrate and an active group of said digestive protein, said linker moiety between said protein and said substrate and covalently linking said protein to a surface of said substrate by an amide bond, the linker moiety between a free amine of said protein and said outer surface of said substrate wherein the digestive protein forms a layer on a surface of said substrate such that the digestive protein is surface exposed for reaction with a stain.

5 Claims, 7 Drawing Sheets

Related U.S. Application Data continuation of application No. 11/562,503, filed on Nov. 22, 2006, now Pat. No. 9,828,597.

(51) Int. Cl.

| | |
|---|---|
| *C09D 5/16* | (2006.01) |
| *C12N 9/20* | (2006.01) |
| *C12N 9/54* | (2006.01) |
| *C12N 9/96* | (2006.01) |
| *C12N 11/04* | (2006.01) |
| *C12N 11/06* | (2006.01) |
| *G06F 21/55* | (2013.01) |
| *G06F 21/56* | (2013.01) |
| *G06F 21/62* | (2013.01) |
| *H04L 9/40* | (2022.01) |

(52) U.S. Cl.
CPC .............. *C09D 5/1687* (2013.01); *C12N 9/20* (2013.01); *C12N 9/54* (2013.01); *C12N 9/96* (2013.01); *C12N 11/04* (2013.01); *C12N 11/06* (2013.01); *C12Y 304/21062* (2013.01); *G06F 21/552* (2013.01); *G06F 21/554* (2013.01); *G06F 21/56* (2013.01); *G06F 21/6218* (2013.01); *H04L 63/1408* (2013.01); *H04L 63/20* (2013.01); *G06F 2221/033* (2013.01); *G06F 2221/034* (2013.01); *G06F 2221/2107* (2013.01); *G06F 2221/2113* (2013.01); *G06F 2221/2145* (2013.01); *H04L 63/06* (2013.01)

(58) Field of Classification Search
CPC .......... C12N 9/96; C12N 11/04; C12N 11/06; C12Y 304/21062
See application file for complete search history.

(56) References Cited

U.S. PATENT DOCUMENTS

| | | |
|---|---|---|
| 3,672,955 A | 6/1972 | Stanley et al. |
| 3,705,938 A | 12/1972 | Hyman |
| 3,857,934 A | 12/1974 | Bernstein et al. |
| 3,935,862 A | 2/1976 | Kraskin |
| 3,957,974 A | 5/1976 | Hata |
| 4,016,043 A | 4/1977 | Schuurs et al. |
| 4,026,814 A | 5/1977 | Johnson et al. |
| 4,034,078 A | 7/1977 | Van Horn |
| 4,094,744 A | 6/1978 | Hartdegen et al. |
| 4,098,645 A | 7/1978 | Hartdegen et al. |
| 4,128,686 A | 12/1978 | Kyle et al. |
| 4,195,127 A | 3/1980 | Hartdegen et al. |
| 4,195,128 A | 3/1980 | Hildebrand et al. |
| 4,195,129 A | 3/1980 | Fukui et al. |
| 4,229,536 A | 10/1980 | DeFilippi |
| 4,237,591 A | 12/1980 | Ginocchio |
| 4,297,137 A | 10/1981 | Sachetto et al. |
| 4,315,828 A | 2/1982 | Church |
| 4,322,308 A | 3/1982 | Hooper et al. |
| 4,385,632 A | 5/1983 | Odelhog |
| 4,539,982 A | 9/1985 | Bailly |
| 4,551,187 A | 11/1985 | Church et al. |
| 4,552,813 A | 11/1985 | Grams |
| 4,897,352 A | 1/1990 | Chonde et al. |
| 4,910,234 A | 3/1990 | Yamamori et al. |
| 5,112,602 A | 5/1992 | Miki et al. |
| 5,279,955 A | 1/1994 | Pegg et al. |
| 5,405,766 A | 4/1995 | Kallury et al. |
| 5,418,146 A | 5/1995 | Joo et al. |
| 5,420,179 A | 5/1995 | Fourquier et al. |
| 5,492,821 A | 2/1996 | Callstrom et al. |
| 5,496,710 A | 3/1996 | Nagao et al. |
| 5,508,185 A | 4/1996 | Kawamura et al. |
| 5,514,671 A | 5/1996 | Lyon et al. |
| 5,523,027 A | 6/1996 | Otsuka |
| 5,543,309 A | 8/1996 | Pischel |
| 5,559,163 A | 9/1996 | Dawson et al. |
| 5,593,398 A | 1/1997 | Weimer |
| 5,595,728 A | 1/1997 | Brockett et al. |
| 5,631,343 A | 5/1997 | Binns et al. |
| 5,643,559 A | 7/1997 | Eigen et al. |
| 5,719,039 A | 2/1998 | Dordick et al. |
| 5,728,544 A | 3/1998 | Tanaka et al. |
| 5,739,004 A | 4/1998 | Woodson |
| 5,739,023 A | 4/1998 | Harada et al. |
| 5,770,188 A | 6/1998 | Hamade et al. |
| 5,800,804 A | 9/1998 | Laney |
| 5,801,140 A | 9/1998 | Langley et al. |
| 5,817,300 A | 10/1998 | Cook et al. |
| 5,837,483 A | 11/1998 | Hirata |
| 5,868,720 A | 2/1999 | Van Antwerp |
| 5,876,802 A | 3/1999 | Brunnemann et al. |
| 5,912,408 A | 6/1999 | Trinh et al. |
| 5,914,367 A | 6/1999 | Dordick et al. |
| 5,919,689 A | 7/1999 | Selvig et al. |
| 5,942,435 A | 8/1999 | Wheeler |
| H1818 H | 11/1999 | Potgieter et al. |
| 5,981,743 A | 11/1999 | Gross et al. |
| 5,998,200 A | 12/1999 | Bonaventura et al. |
| 5,998,512 A | 12/1999 | Schloman |
| 6,030,933 A | 2/2000 | Herbots et al. |
| 6,060,043 A | 5/2000 | Hayden et al. |
| 6,080,391 A | 6/2000 | Tsuchiya et al. |
| 6,107,392 A | 8/2000 | Antonelli et al. |
| 6,150,146 A | 11/2000 | Hamade et al. |
| 6,265,191 B1 | 7/2001 | Mizusawa et al. |
| 6,291,582 B1 | 9/2001 | Dordick et al. |
| 6,303,290 B1 | 10/2001 | Liu et al. |
| 6,342,386 B1 | 1/2002 | Powers et al. |
| 6,472,493 B1 | 10/2002 | Huynh-Ba |
| 6,599,627 B2 | 7/2003 | Yeo et al. |
| 6,638,526 B1 | 10/2003 | Deussen et al. |
| 6,663,949 B1 | 12/2003 | Tanaka et al. |
| 6,713,660 B1 | 3/2004 | Roe et al. |
| 6,759,220 B1 | 7/2004 | LeJeune et al. |
| 6,818,212 B2 | 11/2004 | Johansen et al. |
| 6,844,028 B2 | 1/2005 | Mao et al. |
| 6,855,746 B2 | 2/2005 | Yoshitake et al. |
| 6,875,456 B2 | 4/2005 | Delest et al. |
| 6,881,711 B1 | 4/2005 | Gershun et al. |
| 6,905,733 B2 | 6/2005 | Russell et al. |
| 7,164,037 B2 | 1/2007 | Dietsche et al. |
| 7,211,275 B2* | 5/2007 | Ying .................... A61K 9/143 424/457 |
| 7,335,400 B2 | 2/2008 | Russell et al. |
| 7,632,793 B2 | 12/2009 | Lang |
| 7,687,554 B2 | 3/2010 | Schellenberg et al. |
| 7,932,230 B2 | 4/2011 | McDaniel |
| 7,939,500 B2 | 5/2011 | McDaniel |
| 8,008,180 B2 | 8/2011 | Takahashi et al. |
| 8,011,381 B2 | 9/2011 | Newman et al. |
| 8,011,938 B2 | 9/2011 | Martin et al. |
| 8,222,015 B2 | 7/2012 | Wang et al. |
| 8,252,571 B2 | 8/2012 | Wang et al. |
| 8,311,297 B2 | 11/2012 | Du et al. |
| 8,324,295 B2 | 12/2012 | Jia et al. |
| 8,388,904 B1 | 3/2013 | McDaniel et al. |
| 8,394,618 B2 | 3/2013 | Buthe et al. |
| 8,497,248 B2 | 7/2013 | McDaniel |
| 8,618,066 B1 | 12/2013 | McDaniel |
| 8,796,009 B2 | 8/2014 | Jia et al. |
| 8,932,717 B2 | 1/2015 | Lee et al. |
| 9,012,196 B2 | 4/2015 | Buthe et al. |
| 9,121,016 B2 | 9/2015 | Jia et al. |
| 9,193,873 B2 | 11/2015 | Wang et al. |
| 9,388,370 B2 | 7/2016 | Wu et al. |
| 9,428,740 B2 | 8/2016 | Buthe et al. |
| 9,828,597 B2 | 11/2017 | Wang et al. |
| 2002/0019615 A1 | 2/2002 | Roe et al. |
| 2002/0192366 A1 | 12/2002 | Cramer et al. |
| 2003/0089381 A1* | 5/2003 | Manning, Jr. ......... C11D 11/007 134/1 |
| 2003/0096383 A1 | 5/2003 | Shimizu et al. |
| 2003/0161789 A1 | 8/2003 | Ermantraut et al. |
| 2003/0166237 A1 | 9/2003 | Allermann et al. |

(56) References Cited

U.S. PATENT DOCUMENTS

| | | |
|---|---|---|
| 2004/0009159 A1 | 1/2004 | Polsenski et al. |
| 2004/0063831 A1 | 4/2004 | Sheppard et al. |
| 2004/0067279 A1 | 4/2004 | Delest et al. |
| 2004/0108608 A1 | 6/2004 | Ju et al. |
| 2004/0109853 A1 | 6/2004 | McDaniel |
| 2004/0175407 A1 | 9/2004 | McDaniel |
| 2004/0241497 A1 | 12/2004 | Sasaki et al. |
| 2004/0242831 A1 | 12/2004 | Tian et al. |
| 2004/0259746 A1 | 12/2004 | Warren et al. |
| 2005/0049166 A1 | 3/2005 | Huang |
| 2005/0058689 A1 | 3/2005 | McDaniel |
| 2005/0059128 A1 | 3/2005 | Arnold et al. |
| 2005/0079594 A1 | 4/2005 | Marion |
| 2005/0147579 A1 | 7/2005 | Schneider et al. |
| 2005/0176905 A1 | 8/2005 | Moon et al. |
| 2005/0255078 A1 | 11/2005 | Sakamoto et al. |
| 2005/0272141 A1 | 12/2005 | Crawford |
| 2006/0094626 A1 | 5/2006 | Horton |
| 2007/0093618 A1 | 4/2007 | Cheng et al. |
| 2007/0282070 A1 | 12/2007 | Adams et al. |
| 2008/0038241 A1 | 2/2008 | Schasfoort et al. |
| 2008/0108745 A1 | 5/2008 | Russell et al. |
| 2008/0119381 A1 | 5/2008 | Wang et al. |
| 2008/0145906 A1 | 6/2008 | Boucher et al. |
| 2008/0293117 A1 | 11/2008 | Wang et al. |
| 2008/0319193 A1 | 12/2008 | Grauert et al. |
| 2009/0023859 A1 | 1/2009 | Sakanoue et al. |
| 2009/0045056 A1 | 2/2009 | Berberich et al. |
| 2009/0104086 A1 | 4/2009 | Zax et al. |
| 2009/0238811 A1 | 9/2009 | McDaniel et al. |
| 2009/0274846 A1 | 11/2009 | Wada et al. |
| 2009/0325843 A1 | 12/2009 | Man et al. |
| 2010/0210745 A1 | 8/2010 | McDaniel et al. |
| 2010/0236582 A1 | 9/2010 | Heintz et al. |
| 2010/0248334 A1 | 9/2010 | McDaniel |
| 2010/0269731 A1 | 10/2010 | Tofte Jespersen et al. |
| 2010/0279376 A1 | 11/2010 | Wang et al. |
| 2010/0305014 A1 | 12/2010 | Miralles et al. |
| 2011/0076738 A1 | 3/2011 | Wang et al. |
| 2011/0195035 A1 | 8/2011 | Vondruska et al. |
| 2011/0240064 A1 | 10/2011 | Wales et al. |
| 2011/0250626 A1 | 10/2011 | Williams et al. |
| 2011/0311482 A1 | 12/2011 | Wang et al. |
| 2011/0312057 A1 | 12/2011 | Buthe et al. |
| 2012/0097194 A1 | 4/2012 | McDaniel et al. |
| 2012/0114961 A1 | 5/2012 | Lee et al. |
| 2012/0136119 A1 | 5/2012 | Davis et al. |
| 2012/0208923 A1 | 8/2012 | Jia et al. |
| 2012/0238005 A1 | 9/2012 | Wieland et al. |
| 2012/0276617 A1 | 11/2012 | Jia et al. |
| 2013/0065291 A1 | 3/2013 | Jia et al. |
| 2013/0137159 A1 | 5/2013 | Buthe et al. |
| 2014/0083324 A1 | 3/2014 | Wales et al. |
| 2014/0141490 A1 | 5/2014 | Wang et al. |
| 2014/0193888 A1 | 7/2014 | Souter et al. |
| 2015/0175982 A1 | 6/2015 | Buthe et al. |
| 2015/0191607 A1 | 7/2015 | McDaniel |

FOREIGN PATENT DOCUMENTS

| | | | |
|---|---|---|---|
| AU | 2010201732 A1 | 5/2010 | |
| CA | 2538124 A1 | 12/2004 | |
| EP | 616033 A1 | 9/1994 | |
| EP | 0670380 A1 | 9/1995 | |
| EP | 609691 B1 | 5/1998 | |
| EP | 0896056 A1 | 2/1999 | |
| EP | 1161502 B1 | 12/2004 | |
| EP | 1551927 A1 | 7/2005 | |
| EP | 1609826 A2 | 12/2005 | |
| EP | 1644452 A2 | 4/2006 | |
| EP | 1660596 A1 | 5/2006 | |
| EP | 001661955 A1 | 5/2006 | |
| EP | 2746378 A1 | 6/2014 | |
| FR | 2832145 A1 | 5/2003 | |
| GB | 1518746 A | 7/1978 | |
| GB | 2410249 A | 7/2005 | |
| GB | 2430436 A | 3/2007 | |
| IL | 167413 A | 12/2010 | |
| IL | 174122 A | 9/2011 | |
| IL | 173658 A | 4/2012 | |
| IL | 208769 A | 4/2012 | |
| IL | 214668 A | 1/2013 | |
| IL | 214669 A | 1/2013 | |
| IL | 214670 A | 1/2013 | |
| IL | 214671 A | 1/2013 | |
| IL | 214672 A | 1/2013 | |
| IL | 218129 A | 9/2013 | |
| JP | 86377999 A | 4/1988 | |
| JP | S63171678 A | 7/1988 | |
| JP | S63202677 A | 8/1988 | |
| JP | H01-285188 A | 11/1989 | |
| JP | H0268117 A | 3/1990 | |
| JP | H02-227471 A | 9/1990 | |
| JP | H6-240297 A | 8/1994 | |
| JP | H8-126489 A | 5/1996 | |
| JP | 09-038183 A | 2/1997 | |
| JP | 9-059470 | 3/1997 | |
| JP | 2002526430 A | 8/2002 | |
| JP | 2002-537470 A | 11/2002 | |
| JP | 2002332739 A | 11/2002 | |
| JP | 2004506089 A | 2/2004 | |
| JP | 2009-511072 A | 3/2009 | |
| JP | 2010-510380 A | 4/2010 | |
| JP | 6096748 B2 | 3/2017 | |
| JP | 6192022 B2 | 9/2017 | |
| WO | 89/06278 A1 | 7/1989 | |
| WO | 9516029 A1 | 6/1995 | |
| WO | 9721804 A1 | 6/1997 | |
| WO | WO-9957157 A1 * | 11/1999 | ....... C07K 14/43563 |
| WO | 0050521 A1 | 8/2000 | |
| WO | 200107484 A2 | 2/2001 | |
| WO | 0153010 A1 | 7/2001 | |
| WO | 0216521 A1 | 2/2002 | |
| WO | 2005/026269 A1 | 3/2005 | |
| WO | 2005103372 A2 | 11/2005 | |
| WO | 2007017701 A1 | 2/2007 | |
| WO | 2008000646 A1 | 1/2008 | |
| WO | 2008063902 A2 | 5/2008 | |
| WO | 2009155115 A2 | 12/2009 | |
| WO | 2012110563 A1 | 8/2012 | |

OTHER PUBLICATIONS

Pdf attached of website http://jenalib.leibniz-fli.de/ImgLibDoc/ftir/IMAGE_FTIR.html#:~:text=Amide%20vibrations,-The%20peptide%20group&text=Amide%20I%20and%20amide%20II,related%20to%20the%20backbone%20conformation. (Year: 2022).*

DFT-Calculated IR Spectrum Amide I, II, and III Band Contributions of N-Methylacetamide Fine Components Yan Ji,et al. ACS Omega May 2020 (15), 8572-8578 DOI: 10.1021/acsomega.9b04421. https://www.ncbi.nlm.nih.gov/pmc/articles/PMC7178369/pdf/ao9b04421.pdf (Year: 2020).*

Diane K. Willliams et al., "Analysis of Latent Fingerprint Deposits by Infrared Microspectroscopy", Applied Spectroscopy, vol. 58, No. 3, (2004) pp. 313-316.

E. Roland Menzel, Fingerprint Detection with Lasers, Chapter 7 "Photoluminescence-Based Physical Treatments" Marcel Dekker, Inc. (1999) pp. 155-178.

Edward Bartick et al., "Spectrochemical Analysis and Hyperspectral Imaging of Latent Fingerprints", 16th Meeting of the International Association of Forensic Sciences, (2002) pp. 61-64.

Enzyme Nomenclature 1984, "Recommendations of the Nomenclature Committee of the International Union of Biochemistry on the Nomenclature and Classification of Enzyme-Catalysed Reactions", Academic Press, New York (1984) pp. 270-279.

G L Thomas and T E Reynoldson, "Some observations on fingerprint deposits", 1975 J. Phys. D: Appl. Phys. vol. 8 (1975) pp. 724-729.

Gary Mong et al., "The Chemistry of Latent Prints from Children and Adults", The Chesapeake Examiner, Fall 1999, vol. 37, No. 2, pp. 4-6.

(56) References Cited

OTHER PUBLICATIONS

Geraldine F. Drevon et al.; High-Activity Enzyme-Polyurethane Coatings; (2002) Biotechnology and Bioengineering, vol. 70, No. 7, Inc. pp. 785-794.
J. David Rozzell, "Immobilized Aminotransferases for Amino Acid Production", Methods in Enzymology, vol. 136, (1987) pp. 479-497.
Keiji G. Asano et al., "Chemical Composition of Fingerprints for Gender Determination", J Forensic Sci, Jul. 2002, vol. 47, No. 4.
Kimone M. Antoine, "Chemical Differences are Observed in Children's Versus Adults' Latent Fingerprints as a Function of Time", J Forensic Sci, Mar. 2010, vol. 55, No. 2.
Kostadin Bobev, "Fingerprints and Factors Affecting Their Condition", J. Forensic Ident. 176/45 (2) 1995, pp. 176-183.
Mansfeld et al. Biotechnol. Bioengineer. (2007) 97: 672-679 (Year: 2007).
McDaniel, C.S. et al., "Biocatalytic paints and coatings," ACS Symposium Series (2009), 1002 (Smart Coatings II), pp. 239-249.
Methods in Biotechnology, vol. 17, Microbial Enzymes and Biotransformations, Humana Press, Inc., Totowa, NJ, (2005), Scott J. Novick and J. David Rozzell, "Immobilization of Enzymes by Covalent Attachment".
Mujumder et al. Int. J. Pharma Bio Sci. (2012) 3(1):610-627 (Year: 2012).
Novick, S. et al.; Protein-containing hydrophobic coatings and films, Biomaterials, 23: 441-448, 2002.
Ramotowski, R.S., in Advances in Fingerprint Technology, Chapter 3, Henry C Lee and R.E. Gaensslen, eds., CRC Press, Boca Raton, (2001) pp. 63-104.
*Reactive Surfaces* v. *Toyota Motor Corporation*, Case IPR2016-01462, Paper No. 51 (PTAB, Jan. 12, 2018).
*Reactive Surfaces* v. *Toyota Motor Corporation*, Case IPR2016-01914, Paper No. 64 (PTAB, Mar. 1, 2018).
*Reactive Surfaces* v. *Toyota Motor Corporation*, Case IPR2017-00572, Paper No. 42 (PTAB, Feb. 5, 2018).
Robert D. Olsen, Sr., "Chemical Dating Techniques for Latent Fingerprints: A Preliminary Report", Identification News, (Feb. 1987) pp. 10-12.
Robert D. Olsen, Sr., "Scott's Fingerprint Mechanics" Chapter III, "Latent Fingerprints and Crime Scene Procedures", (1978) pp. 109-158.
Robert S. Ramotowski, Advances in Fingerprint Technology (2nd ed.), Chapter 3, "Composition of Latent Print Residue", In H.C. Lee and R.E. Gaensslen (Eds), Boca Raton: CRC Press, (2001) pp. 63-104.
Roberts, "Chemistry for peptide and protein PEGylation", Advanced Drug Delivery Reviews, vol. 54, 2002, p. 459-476.
S.M. Bleay et al., "Fingerprint Source Book: manual of development techniques", London: Home Office—Centre for Applied Sciences and Technology. Chapter 2: Finger mark examination techniques within scope of ISO 17025, pp. 3-38 (2013) URL: http://www.gov.uk/government/publications/fingerprint-source-book.
Science News Staff, "Fleeting Fingerprints May Yield Powerful New Tools", Apr. 15, 1997.
Sookkheo et al., Protein Expression and Purification (2000) 20: 142-151.
T. Kent (Ed.), Manual of Fingerprint Development Techniques—A Guide to the Selection and Use of Processes for the Development of Latent Fingerprints, 2nd Ed 1998 (Revised Jan. 2001), Sandridge: Home Office Police Scientific Develpment Branch, Chapter 1 "Latent Fingerprints", Sections 1.1, 1.2, 2.6 and "Visual Examination".
U.S. Appl. No. 12/643,666, filed Dec. 21, 2009.
United States Department of Justice—Federal Bureau of Investigation, "The Science of Fingerprints—Classification and Uses", (Rev. 12-84), Chapter XIII "Latent Impressions" pp. 170-174 (1985).
Young Duk Kim et al., "Siloxane-Based Biocatalytic Films and Paints for Use as Reactive Coatings", Biotechnology and Bioengineering, vol. 72, No. 4, Feb. 20, 2001, pp. 475-482.
Mansfeld, "The Stability of Engineered Thermostable Neutral Proteases from Bacillus Stearothermophilus in Organic Solvents and Detergents", Biotechnol. Bioeng. (2007) 97 (4): 672-679.
Bernfield, P. and Wan, J., "Antigens and Enzymes Made Insoluble by Entrapping Them into Lattices of Synthetic Polymers", Science 142 (3593), pp. 678-679 (1963).
Pollak et al., "Enzyme Immobilization by Condensation Copolymerization into Cross-Linked Polyacrylamide Gels", J. Am. Chem. Soc. 1980, 102, pp. 6324-6336.
Fukui et al., "Application of Photo-Crosslinkable Resin to Immobilization of an Enzyme", FEBS Letters, Jul. 1976, pp. 179-182, vol. 66, No. 2.
Fukui et al., "[20] Entrapment of Biocatalysts with Photo-Cross-Linkable Resin Prepolymers and Urethane Resin Prepolymers", Methods in Enzymology, vol. 135, 1987, pp. 230-252.
K. Yokozeki et al., "Application of Immobilized Lipase to Regio-Specific Interesterification of Triglyceride in Organic Solvent", European J Appl Microbiol Biotechnol (1982) 14:1-5.
Fusee, Murray C., "[42] Industrial Production of L-Aspartic Acid Using Polyurethane-Immobilized Cells Containing Aspartase", Methods in Enzymology, vol. 136, 1987, pp. 463-471.
G.J. Calton et al., "[45] Phenylalanine Production via Polyazetidine-Immobilized *Escherichia coli*: Optimization of Cell Loading" Methods in Enzymology, vol. 136, 1987, pp. 497-502.
Takagi, Toshio, "Confirmation of Molecular Weight of Aspergillus oryzae a-Amylase Using the Low Angle Laser Light Scattering Technique in Combination with High Pressure Silica Gel Chromatography", J. Biochem. vol. 89, No. 2, (1981), pp. 363-368.
E.A. Stein et al., "Alpha-Amylases as Calcium-Metalloenzymes. I. Preparation of Calcium-free Apoamylases by Chelation and Electrodialysis", Biochemistry, vol. 3, No. 1, Jan. 1964, pp. 56-61.
G. Muralikrishna et al., "Cereal a-amylases—an overview", Carbohydrate Polymers 60 (2005) pp. 163-173.
C.P. Poole, Jr. et al., "Introduction to Nanotechnology", John Wiley & Sons, 2003, Hoboken, NJ, Table 12.1 on p. 315.
L.R. Murphy et al., "Research Paper Protein hydraftion and unfolding", Folding & Design vol. 3, No. 2, 1998, pp. 105-118.
K. Won et al., "Effects of Water and Silica Gel on Enzyme Agglomeration in Organic Solvents", Biotechnol. Bioprocess Eng. 2001, vol. 6, No. 2, pp. 150-155.
R. Balasubramanian et al., "Extraction and Dispersion of Large Gold Nanoparticles in Nonpolar Solvents", J. Dispersion Science and Technology, vol. 22, No. 5, pp. 485-489 (2001).
M.S. Kunz et al., "Colloidal Gold Dispersions in Polymeric Matrices", Journal of Colloid and Interface Science 156, pp. 240-249 (1993).
A. Gole et al., "Pepsin-Gold Colloid Conjugates: Preparation, Characterization, and Enzymatic Activity", Langmuir 2001, 17, pp. 1674-1679.
A. Gole et al., "Studies on the formation of bioconjugates of Engoglucanase with colloidal gold", Colloids and Surfaces B: Biointerfaces 25 (2002) pp. 129-138.
Product Sheet by Novozymes A/S for Termamyl 120L, Type L pp. 1:4-4:4 (2002).
Johanna Mansfeld et al.; Site-specific and random immobilization of thermolysin-like proteases reflected in the thermal inactivation kinetics; Biotechnol. Appl. Biochem. (2000); pp. 189-195.
Minoru Kumakura et al.; 201. Interaction of Enzyme with Polymer Matrix in Immobilized Enzymes; Helvetica Chimica Acta; vol. 66; Fasc. 7; (1983); pp. 2044-2048.
Jaroslava Turková; Immobilization of Enzymes on Hydroxyalkyl Methacrylate Gels; Immobilization Techniques; Methods in Enzymology; (1976); 344: pp. 66-83.
Masahiro Takagi et al.; Nucleotide Sequence and Promoter Region for the Neutral Protease Gene from *Bacillus stearothermophilus*; Journal of Bacteriology, Sep. 1985, pp. 824-831.
Kuniyo Inouye et al.; Engineering, expression, purification, and production of recombinant thermolysin; Biotechnology Annual Review; vol. 13; ISSN 1387-2656; pp. 43-64 (2007).
Drevon, G. et al.; High-Activity Enzyme-Polyurethane Coatings, Biotechnology and Bioengineering, 79(7): 785-794, Sep. 30, 2002.

(56) References Cited

OTHER PUBLICATIONS

Mansfeld, et al.: The Stability of Engineered Thermostable Neutral Proteases from Bacillus Stearothermophilus in Organic Solvents and Detergents, Biotechnol. Bioeng. (2007) 97 (4): 672-679.
U.S. Appl. No. 14/093,347, filed Nov. 29, 2013.
U.S. Appl. No. 14/097,128, filed Dec. 4, 2013.
Drevon, Géraldine F., "Enzyme Immobilization into Polymers and Coatings", University of Pittsburgh School of Engineering Dissertation, Nov. 2002.
Lt Col C. Carl Bostek, "Effective methods of in-line intravenous fluid warming at low to moderate infusion rates" Journal of the American Association of Nurse Anesthetists, vol. 60, No. 6, Dec. 1992.
McDaniel, Steve et al., "Functional Additives: A Platform for Revitalizing the Paint and Coatings Industry", coatingsworld.com, Feb. 2010.
McDaniel, Steve, "Formulating with Bioengineered Additives: Enhancing the Performance and Functionality of Paints and Coatings", coatingsworld.com, Mar. 2010.
McDaniel, Steve, "Bioengineered Additives A Pipeline of Value Delivering Unique Functionality to Your Coating", Coatings World, vol. 15, No. 5, coatingsworld.com, May 2010.
Ciba Tinuvin 328 Light Stabiliser, Ciba Specialty Chemicals Inc., Coating Effects Segment, Edition: Dec. 9, 1997 Basle.
Ciba Tinuvin 1130, Ciba Specialty Chemicals Inc., Coating Effects Segment, Edition: Dec. 15, 1997 Basle.
"Printing & Packaging Industrial Coatings Technical Data Sheet Tinuvin 400" BASF The Chemical Company, Dec. 2010 Rev 1.
R. Lambourne and T.A. Strivens (Editors), "Paint and surface coatings—Theorgy and practice" second edition, "5.18 Ultraviolet absorbers", 1999, pp. 195-196, William Andrew Publishing.
Dieter Stoye and Werner Freitag (Editors) "Paints, Coatings and Solvents", Second, Completely Revised Edition, "5. Paint Additives", 1998, p. 170, Wiley VCH.
Johan Bieleman (Editor), "Additives for Coatings", "8,2,3 Properties of Light Stabilizers", 2000, pp. 279-280, Wiley VCH.
H. Domininghaus, "Plastics for Engineers: Materials, Properties, Applications", 1993, p. 612, Carl Hanser.
Ruby Ynalvez et al., "Mini-review: toxicity of mercury as a consequence of enzyme alternation", Biometals (2016) 29: 781-788.
Manuela F. Frasco et al., "Mechanisms of cholinesterase inhibition by inorganic mercury", FEBS Journal 274 (2007) 1849-1861.
S. Gourinath et al. "Mercury induced modifications in the stereochemistry of the active site through Cys-73 in a serine protease—Crystal structure of the complex of a partially modified proteinase K with mercury at 1.8 Å resolution", Indian Journal of Biochemistry & Biophysics, vol. 38, Oct. 2001, pp. 298-302.
Annamaria Guagliardi et al., "Stability and activity of a thermostable malic enzyme in denaturants and water-miscible organic solvents" Eur. J. Biochem. 183, 25-30 (1989).
H.N. Fernley and P.G. Walker, "Studies on Alkaline Phosphatase: Inhibition by Phosphate Derivatives and the Substrate Specificity" Biochem. J. (1967) 104, 1011-1018.
Defoamer Technologies Agitanò, Münzing, PCA Apr. 2012.
Jose L. Muñoz-Muñoz et al., "Phenolic substrates and suicide inactivation of tyrosinase: kinetics and mechanism", Biochem. J. (2008) 416, 431-440.
Travis J. O'Brien et al., Effects of hexavalent chromium on the survival and cell cycle distribution of DNA repair-deficient S. cerevisiae, DNA Repair 1 (2002) 617-627, Elsevier.
Joan L. Huber et al., "Inactiviation of Highly Activated Spinach Leaf Sucrose-Phosphate Synthase by Dephosphorylation", Plant Physiol. (1991) 95, 291-297.
J.M. Widholm et al., "Inhibition of Cultured Cell Growth by Tungstate and Molybdate", Plant Cell Reports (1983) 2: 15-18, Springer-Verlag.

K.J. Lewis, J.H. Aklian, A. Sharaby, J.D. Zook, "Quantitative methods of predicting relative effectiveness of corrosion inhibitive coatings", Aircraft Engineering and Aerospace Technology, (1996) vol. 68 Issue: 3, pp. 12-22.
K.D. Ralston et al., "Electrochemical Evaluation of Constituent Intermetallics in Aluminum Alloy 2024-T3 Exposed to Aqueous Vanadate Inhibitors", Journal of The Electrochemical Society, 156 (4) C135-C146 (2009).
David B. Volkin, Henryk Mach and C. Russell Middaugh, "Review: Degradative Covalent Reactions Important to Protein Stability", Molecular Biotechnology 105, vol. 8, pp. 105-121 (1995).
"Emulsion Stability and Testing", Technical Brief 2011 vol. 2, Particle Sciences, Inc.
Solvent Miscibility Table / Solvent Polarity Chart (2013).
Muxin Liu, Michael A. Brook, Paul M. Zelisko and Amro N. Ragheb, "Chapter 11. Preparation and Applications of Silicone Emulsions Using Biopolymers", Colloidal Biomolecules, Biomaterials, and Biomedical Applications (2003).
Roman Pichot, "Stability and Characterisation of Emulsions in the presence of Colloidal Particles and Surfactants" A thesis submitted to the University of Birmingham for the degree of Doctor of Philosophy, Nov. 2010.
Wang, P. et al, Enzyme Stabilization by Covalent Binding in Nanoporous Sol-Gel Glass for Nonaqueous Biocatalysis; Biotech. Bioeng. 2001, 74(3):249-255.
Kim Y. et al, Siloxane-based biocatalytic films and paints for use as reactive coatings, Biotechnology and Bioengineering 2001, 72(4), 475-482.
"Enzyme Nomenclature—Recommendations (1978) of the Nomenclature Committee of the international Union of Biochemistry", Academic Press, New York, (1979) pp. 234-239.
A. Dorinson et al, "Refractive Indices and Densities of Normal Saturated Fatty Acids in the Liquid State", J. Am. Chem. Soc., 1942, 64(12), pp. 2739-2741.
Anil K. Jain et al., "Integrating Faces, Fingerprints, and Soft Biometric Traits for User Recognition", Proceedings of Biometric Authentication Workshop, LNCS 3087, pp. 259-269,Prague, May 2004.
Arthur and Elizabeth Rose, "The Condensed Chemical Dictionary (7th Ed.)", New York: Reinhold Publishing Co., pp. 80, 104, 222-223, 545, 556, 644-645, 691, 704, 716, 887, 891 (1961).
B. Drozdowski et al.,. "Isopropyl Alcohol Extraction of Oil and Lipids in the Production of Fish Protein Concentrate from Herring", Journal of the American Oil Chemists' Society, (Jul. 1969) vol. 46, pp. 371-376.
B. Scruton et al, "The deposition of fingerprint films" 1975 J. Phys. D: Appl PHys. 8 pp. 714-723.
B.M. Craig, "Refractive Indices of Some Saturated and Monoethenoid Fatty Acids and Methyl Esters", Canadian Journal of Chemistry, 1953, 31(5): pp. 499-504, https://doi.org/10.1139/v53-068.
David Rozzell and Fritz Wager (Eds), Biocatalytic Production of Amino Acids & Derivatives, Chapter 13 "Immobilized Enzymes: Techniques & Applications", Hanser Publishers (1992), pp. 306-319.
Deliang He et al., a-Amylase immobilized on bulk acoustic-wave sensor by UV-curing coating, Biochemical Engineering Journal 6 (2000) 7-11.
G.W. Xing et al., "Influence of reaction conditions on syntheses of sweetener precursors catalyzed by thermolysin in tert-amyl alcohol", J. Peptide Res. vol. 52, Issue 4, pp. 300-304 (Date: 1998).
A. Koohestanian et al., "The Separation Method for Removing of Colloidal Particles from Raw Water", American-Eurasian J. Agric. & Environ. Sci., 4 (2): pp. 266-273 (2008).
W. Stöber et al., "Controlled Growth of Monodisperse Silica Spheres in the micron Size Range", Journal of Colloid and Interface Science 26, pp. 62-69 (1968).
M. Melchiors et al., "Recent developments in aqueous two-component polyurethane (2K-PUR) coatings", Progress in Organic Coatings 40 (2000), pp. 99-109, p. 100, first complete paragraph.
N.F. Almeida et al., "Immobilization of Glucose Oxidase in Thin Polypyrrole Films: Influence of Polymerization Conditions and

(56) References Cited

OTHER PUBLICATIONS

Film Thickness on the Activity and Stability of the Immobilized Enzyme", Biotechnology and Bioengineering, vol. 42, pp. 1037-1045 (1993).
Green, Philip, "Fineness of Grind", European Coatings Journal, (2003), Issue 10, p. 53.
Third-Party Submission Under 37 CFR 1.290 dated Aug. 13, 2018 filed in U.S. Appl. No. 15/790,846, filed Oct. 23, 2017.
Third-Party Submission Under 37 CFR 1.290 dated Jul. 25, 2018 filed in U.S. Appl. No. 15/810,700, filed Nov. 13, 2017.
Third-Party Submission Under 37 CFR 1.290 dated Jul. 25, 2018 filed in U.S. Appl. No. 15/810,713, filed Nov. 13, 2017.
Non-Final Office Action dated Jan. 14, 2015 for U.S. Appl. No. 14/166,376.
Office Action Response filed Apr. 14, 2015 for U.S. Appl. No. 14/166,376.
Final Office Action dated Apr. 27, 2015 for U.S. Appl. No. 14/166,376.
Notice of Appeal and Pre-Brief Conference Request filed on Jun. 26, 2015 for U.S. Appl. No. 14/166,376.
Pre-Brief Appeal Conference Decision dated Jul. 21, 2015 for U.S. Appl. No. 14/166,376.
Notice of Allowance and Notice of Allowability dated Jul. 24, 2015 for U.S. Appl. No. 14/166,376.
*Reactive Surfaces v. Toyota Motor Corporation*, Case IPR2018-01194 filed Jun. 4, 2018, Petition for Inter Partes Review of U.S. Pat. No. 9,193,873 B2 with Declaration and Resume of Dr. David Rozzell, Ph.D.
"Enzyme Nomenclature—Recommendations (1978) of the Nomenclature Committee of the international Union of Biochemistry", Academic Press, New York, (1979) pp. 274-277.
*Reactive Surfaces v. Toyota Motor Corporation*, Case IPR2017-00572, Paper No. 42 (PTAB, Feb. 5, 2017).
Office Action Response filed Apr. 27, 2015 for U.S. Appl. No. 14/097,128.
Amendment and RCE Response filed Aug. 26, 2015 for U.S. Appl. No. 14/097,128.
Rebuttal document produced during oral deposition of Douglas Lamb, Ph.D.; May 10, 2017.
OMG Borchers GmbH; "Low molecular weight methyl polysiloxane for improved leveling and anti-float properties in solvent based coatings systems. 100% active"; Jul. 1, 2014.
OMG Borchers GmbH; "Low molecular weight methyl polysiloxane for improved leveling and anti-float properties in solvent based coatings systems. 100% active ingredient"; Aug. 28, 2009.
Reply Declaration of Eric Ray; Nov. 6, 2017.

*Reactive Surfaces v. Toyota Motor Corporation*, Case IPR2019-00867, Petition for Inter Partes Review of U.S. Pat. No. 9,428,740 B2, PTAB (Mar. 21, 2019).
Michelle V. Buchanan et al., "Chemical Characteristics of Fingerprints from Adults and Children," in Forencsic Evidence Analysis & Crime Scene Investigation, 2941 Proc. SPIE 89 (Feb. 5, 1997).
G.M. Mong et al. "Advanced Fingerprint Analysis Project Fingerprint Constituents," Technical Report, Pacific Northwest Laboratory (1999).
The American Heritage STEDMAN'S Medical Dictionary, Second Edition, (Copyright 2007 and 2004, Houghton Mifflin), pp. 463-464, 884.
K. Hans Brockerhoff et al., "Lipolytic Enzymes", Academic Press, Inc., New York, New York, 1974, pp. 1-2, 4 and 8.
Shigeru Yamanaka et al., "[37] Regiospecific Interesterification of Triglyceride with Celite-Adsorbed Lipase," Methods in Enzymology, vol. 136, pp. 405-411 (1987).
Kiyotaka Oyama et al., "[46] Production of Aspartame by Immobilized Thermoase", Methods in Enzymology vol. 136, pp. 503-516 (1987).
Bo Chen et al., "Candida antarctica Lipase B Chemically Immobilized on Epoxy-Activated Micro- and Nanobeads: Catalysts for Polyester Synthesis", Biomacromolecules (published Jan. 16, 2008), vol. 9, Issue 2, pp. 463-471.
K. Bagi et al., "Immobilization and characterization of porcine pancreas lipase", Eyzyme and Microbial Technology vol. 20, pp. 531-535 (1997).
Recorded Assignment Documentation for U.S. Appl. No. 14/643,445, filed Mar. 10, 2015 (Exhibit 1003 from IPR2019-00867).
Declaration of Dr. David Rozzell, Ph.D. (Exhibit 1009 from IPR2019-00867)—May 14, 2018.
Non-Final Office Action dated Sep. 25, 2015 from U.S. Appl. No. 14/643,445, filed Mar. 10, 2015.
Office Action Response filed Dec. 29, 2015 from U.S. Appl. No. 14/643,445, filed Mar. 10, 2015.
Notice of Allowance and Notice of Allowability dated Apr. 28, 2016 from U.S. Appl. No. 14/643,445, filed Mar. 10, 2015.
As-filed U.S. Appl. No. 12/820,063, filed Jun. 21, 2010.
Deposition Transcript of Dr. Jonathan S. Dordick from IPR2016-01914 (Exhibit 1015 from IPR2019-00867)—Oct. 18, 2017.
Yang et al. Biotechnol Lett. Jul. 2010: 32(7): 951-6. Epub Mar. 8, 2010 (Year: 2010).
Chen et al. Biomacromolecules. Feb. 2008: 9(2): 463-71. Epub (Year: Jan. 16, 2008).
Yu et al. Biotechnol Lett. Apr. 2004; 26(8): 629-33 (Year: 2004).

\* cited by examiner

Physical Adsorption     Covalent Crosslinking

BIOFUNCTIONAL MATERIALS

CROSS REFERENCE TO RELATED APPLICATIONS

This application is a continuation of U.S. patent application Ser. No. 15/790,846 filed Oct. 23, 2017, which is a continuation of U.S. patent application Ser. No. 11/562,503 filed Nov. 22, 2006, the entire contents of each of which are incorporated herein by reference.

FIELD

The present disclosure relates to self-cleaning compositions and a process for preventing and reducing surface stain accumulation due to bird droppings, bug wastes, food debris, and other stain causing materials.

TECHNICAL BACKGROUND

Both interior and exterior surfaces of automobile, such as coatings, paints, and seat fabrics, are subject to contamination and corrosions when they are under prolonged exposure to bird dropping, insect debris, resins of conifer, microbes, gums, etc. Certain stains, such as insect-originated stains, are hard to remove with regular automatic brush-free washing. Interior surfaces and coatings may also be easily get stained with oil, protein, sugar and other ingredients in foods and beverages, and timely removal of such stains may present certain challenges.

Here, the present invention specifically involves the incorporation of digestive proteins including lysozymes, proteases, lipases, cellulases, etc., onto surfaces such as paints and coatings. The catalytic activity of the digestive proteins enables ongoing self-cleaning to reduce and eliminate stain contaminations. The mechanism of action of these digestive proteins is mainly enzymatic in nature and does not involve the use of any corrosive or oxidative components; therefore, they are environmentally friendly.

Stains of interests in the initial stage of this work include those formed from broken bodies of bugs, animal (like bird) wastes, foods, milk and other beverages, and cosmetic and personal care products. Although the detailed components vary with sources of stains, the major components of stains that are adhesive to surfaces are proteins, polysaccharides, fats or oils.

DESCRIPTION OF RELATED ART

It is known to incorporate enzymes into coating or into substrates for the purpose of providing a surface with antimicrobial, antifungal or antifouling properties. Yet it is novel to the best knowledge of Applicants to attach digestive proteins to a surface for the purpose of enzymatically decomposing stain molecules in contact with the surface.

U.S. Pat. No. 6,818,212 discloses an enzymatic antimicrobial ingredient for disinfection and for killing microbial cells.

Wang et al. 2001 discloses lifespan extension of an enzyme upon its covalent binding at wet conditions; yet the reference does not seem to mention the utilization of such covalently bound enzyme in the area of surface self-cleaning.

U.S. Pat. No. 3,705,398 discloses polymeric articles having active antibacterial, antifungal and combinations of antibacterial and antifungal properties. The antibacterial and antifungal activating agents are distributed within the polymeric composition and migrate to the surface.

U.S. Pat. No. 5,914,367 discloses a method of preparing a polymer-protein composite including polymerizing a monomer in the presence of a protein dissolved in an organic phase via the ion-pairing of the protein with a surfactant. This reference, however, does not seem to mention the prevention or reduction of stain accumulation using the digestive power of such a polymer-protein composite.

U.S. Pat. No. 6,150,146 discloses a method of releasing a compound having antimicrobial activity from a matrix at a controlled rate. The method includes an enzyme and a substrate within the matrix beforehand to allow the enzyme and substrate to react with each other in the matrix, thereby to produce a compound having antimicrobial activity. The patent also discloses a coating composition comprising a film-forming resin, an enzyme, a substrate and any enzyme capable of reacting with the substrate.

U.S. 2005/0058689 discloses paints and coatings having antifungal growth and antibacterial materials. Specific chemicals and formations are disclosed for incorporation into painted surfaces which are antifungal compositions to inhibit growth of mold, bacterial, and fungi on building materials.

The object of the present invention is to provide self-cleaning composition and process containing digestive proteins for preventing and reducing stain accumulation.

SUMMARY

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

Provided are compositions for self-cleaning of a stain that include a substrate, a digestive protein capable of decomposing a stain molecule, and a linker moiety between the substrate and the digestive protein, where the linkage is or is between a free amine on the digestive protein and the substrate.

The compositions as provided herein may be useful as a mechanism to prevent the accumulation of contacting stains and dirt by an "automatic" enzymatic degradation reaction. The digestive proteins of the composition may include proteases which hydrolyze protein molecules, lipases which hydrolyze lipids and fats, cellulases which hydrolyze cellulose, and amylases which hydrolyze carbohydrates, etc. It is neither required nor necessary for the digestive proteins to have their functional binding pockets all facing towards stain particles. A layer of digestive proteins delivers enough coverage and digesting activity even though the digestive proteins may be randomly arranged on a surface.

Optionally, a surface may be pretreated with a layer of polymer comprising one or more active groups. A digestive protein suspension may be spin coated onto the polymer layer with the active groups to form covalent bonds between the proteins and the polymer layer. The active groups may comprise alcohol, thiol, aldehyde, carboxylic acid, anhydride, epoxy, and ester, etc. Alternatively, digestive proteins may be attached to nanoparticles before their suspension with paints or coatings.

BRIEF DESCRIPTION OF DRAWINGS

The present invention is further illustrated by reference to the accompanying drawings, in which.

DETAILED DESCRIPTION

Figure 1:
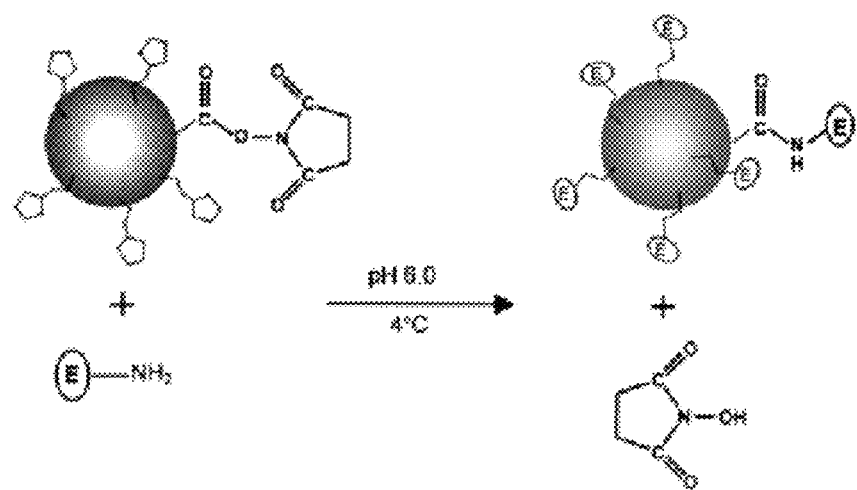
FIG. 1 is a depiction of an attachment of enzymes to the surface of polymeric nanoparticles.

The present disclosure relates to, in a first aspect, a composition comprising a substrate, a digestive protein capable of decomposing a stain molecule, and a linker moiety.

This disclosure specifically involves the incorporation of one or more digestive proteins including lysozymes, proteases, lipases, cellulases, etc., onto surfaces such as paints and coatings. The catalytic activity of the digestive proteins enables ongoing self-cleaning to reduce and eliminate stain contaminations.

Various stains include those formed from broken bodies of bugs, animal (such as bird) wastes, foods, milk and other beverages, and cosmetic and personal care products. Although the detailed components vary with sources of stains, the major components of stains that are adhesive to surfaces are proteins, polysaccharides, fats or oils.

The activity of the digestive proteins toward different stain sources may be evaluated in a solution environment. Tests are conducted at different conditions including different pH and temperature, in an attempt to evaluate the proteins' performance in an automobile environment instead of that in a washer machine as they have been traditionally applied. Tests include: protein-related activity; starch-related activity tests; tests with oily stains. Protein activity unit is defined as: one unit of digestive protein hydrolyzes casein to produce absorbance difference equivalent to 1.0 µmol of tyrosine per minute at 37° C. under the conditions of the assay. Results of activity assay show covalent cross-linked protease present an activity that is nine times more than that of a physically absorbed protease.

There are several ways to incorporate the digestive proteins onto a substrate. One of which involves the application of covalent bonds. Specifically, free amine groups of the digestive proteins may be covalently bound to an active group of the substrate. Such active groups include alcohol, thiol, aldehyde, carboxylic acid, anhydride, epoxy, ester, or any combination thereof. This method of incorporating digestive proteins delivers unique advantages. First, the covalent bonds tether the proteins permanently to the substrate and thus place them as an integral part of the final composition with much less, if not at all, leakage of digestive protein species. Second, the covalent bonds provide for extended enzyme lifetime. Over time, proteins typically lose activity because of the unfolding of their polypeptide chains. Chemical binding such as covalent bonding effectively restricts such unfolding, and thus improves the protein life. The life of a protein is typically determined by comparing the amount of activity reduction of a protein that is free or being physically adsorbed with that of a protein covalently-immobilized over a period of time. Results have shown that a protein that is in free form or being physically adsorbed to a substrate loses its activity much faster that a protein in covalent-bond form.

Alternatively, digestive proteins may be uniformly dispersed throughout the substrate network to create a homogenous protein platform. In so doing, digestive proteins may be first modified with polymerizable groups. The modified proteins may be solubilized into organic solvents in the presence of surfactant, and thus engage the subsequent polymerization with monomers such as methyl methacrylate (MMA) or styrene in the organic solution. The resulted composition includes digestive protein molecules homogeneously dispersed throughout the network.

Also, digestive proteins may be attached to surfaces of a substrate in comparison to the above mentioned cross-linking methods. An attachment of digestive proteins corresponding to ~100% surface coverage was achieved with polystyrene particles with diameters range from 100 to 1000 nm.

The digestive proteins of the composition may include proteases which hydrolyze protein molecules, lipases which hydrolyze lipids and fats, cellulases which hydrolyze cellulose, and amylases which hydrolyze carbohydrates. It is neither required nor necessary for the digestive proteins to have their functional binding pockets all facing toward stain particles. A layer of digestive proteins delivers enough coverage and digesting activity even though the digestive proteins may be randomly arranged on a surface.

Optionally, a surface is pretreated with a layer of polymer comprising one or more surface active groups of succinimide ester. A digestive protein suspension is spin coated onto the layer of the polymer with the active groups to form covalent bonds with the proteins. Alternatively, digestive proteins may be attached to nanoparticles before their suspension with paints or coatings.

This disclosure is further directed to a composition comprising a digestive protein capable of decomposing a stain molecule, and a coating substrate wherein the digestive protein may be entrapped in the coating substrate. In this composition, the digestive protein may be selected from lysozymes, proteases, lipases, cellulases, glycosidases, and amylases.

In another aspect of this disclosure, a process is disclosed for reducing and or eliminating stain contaminations. The process comprises binding a substrate to a surface and forming a linker moiety between an active group of a digestive protein and the substrate. In this process, the substrate may comprise surface active groups such as alcohol, thiol, aldehyde, carboxylic acid, anhydride, epoxy, ester, and any combinations thereof.

Example 1

Enzymes may be attached to surfaces of plastics. An enzyme attachment corresponding to ~100% surface coverage may be achieved with polystyrene particles with diameters range from 100 to 1000 nm. By coating with digestive protein, these particles may be used along with paints or coatings to functionalize the surfaces of materials. The same chemical bonding approach may be applied to coat enzymes onto preformed plastic parts, and thus form a protein coating on the parts' surfaces. As shown in FIG. 1, particles with diameters ranging from 100 nm to 1000 nm may be synthesized by emulsion polymerization. Emulsion polymerization is a type of polymerization that takes place in an emulsion typically incorporating water, monomer, and surfactant. The most common type of emulsion polymerization is an oil-in-water emulsion, in which droplets of monomer (the oil) are emulsified (with surfactants) in a continuous phase of water.

Particles as previously described may be synthesized by mixing an aqueous solution (mixture of water and ethanol, ~20 ml), containing a polymerizable surfactant (2-sulfoethylmethacrylate), a stabilizer (polyvinylpyrrolidone, PVP) and an initiator (2,2'-Azobis [2-methyl-N-(2-hydroxyethyl) propionamide]), will be mixed with an organic solution (~1 ml) of styrene, N-acryloxysuccinimide (NAS, a functionalized vinyl monomer), and divinyl benzene (~1% v/v). The particle size may be controlled by adjusting phase ratio (1/30~1/15, oil/aqueous) and the concentration of ethanol (0.125~0.50 ml/ml), 2-sulfoethyl methacrylate and PVP (0~5.5 mg/ml). The reaction may be performed with stirring at 70° C. for 10 h, followed by washing the resulted particles with ethanol and DI water in a stirred ultrafiltration cell with a polyethersulfone membrane (cut off MW: 300 kDa).

Example 2

Stains may be generated from different sources of contacts. Body residues of bugs, animal wastes, food, milk and other beverages, and cosmetic and personal care products may all cause stains. Although the detailed components vary with sources of stains, the major components that are adhesive to surfaces are proteins, simple sugars and polysaccharides, fats and/or oils. Digestive proteins including lipases, proteases, amylase and cellulose, each of them attacks different components, are thus far the most effective, safe and economic agents to fight against such stains. As shown below in Table 1, these proteins were examined and tested in our initial screening tests, and eventually we selected protease to proceed for the majority of the subsequent experiments due to the easiness in activity measurement.

TABLE 1

| Enzyme | Targeting Stains | Source | Functions | Standard testing conditions |
|---|---|---|---|---|
| Proteases | Bugs, dairy products, animal wastes | *Bacillus licheniformis* (Subtilisin Carlsberg) | Hydrolysis of proteinaceous materials | Casein with Folin & Ciocalteu's Phenol dye, pH 7.5, 37° C., absorbance at 660 nm |
| Lipase AK | Fats and oils, cosmetics, inks | *Pseudomonas fluorescens* | Hydrolysis of oils and fats | p-nitro phenyl valerate, pH 7.7, 40° C., absorbance at 405 nm |
| α-Amylase | Juices, soft drinks, foods, animal wastes | *Bacillus subtilis* | Hydrolysis of starch | Dyed Starch, pH 6.9, 25° C., absorbance at 540 nm |
| Cellulase | Beverages, foods, animal wastes, | *Aspergillus niger* | Hydrolysis of cellulose | Dyed cellulose, pH 6, 50° C., absorbance at 590 nm |

Example 3

Preparation of Enzyme Coating

N-acryloxy succinimide (392 mg), 1.2 ml of styrene and 29.2 mg of 4,4'-azobis-(4-cyanovaleric acid) were mixed with 16 ml of chloroform in a 20 ml glass reaction vial. The vial was purged with nitrogen, sealed and incubated at 70° C. for 12 hrs with stirring, followed by the removal of solvent by purging nitrogen. The polymer product was re-dissolved in chloroform at a concentration of 50 mg/ml. One milliliter of the resulting solution was spin-coated onto a polystyrene plate (11 cm in diameter) at 6000 rpm. Protease from Subtilisin Carlsberg was dissolved in 0.05 M phosphate buffer at a concentration of 10 mg/ml. The enzyme was applied onto the active polymer coated plate via 3-step layer-by-layer spin coating: 1) 1 ml of the protease solution, 2) 1 ml of protease solution containing 0.5% (V/V) of glutaraldehyde, 3) 1 ml of protease solution. The spin-coated plates were kept at 4° C. for 12 h, followed by extensive washing with 0.05 M Tris buffer (pH 8), 2M NaCl solution and DI water. Finally the plates were air-dried and cut into small pieces (1×2 cm). This method was designated as covalent cross-linking. As a comparison, similar procedure was applied on a polystyrene plate without the active polymer coating, which was called as physical adsorption.

Example 4

Visualization of Enzyme Coating

Figure 2:
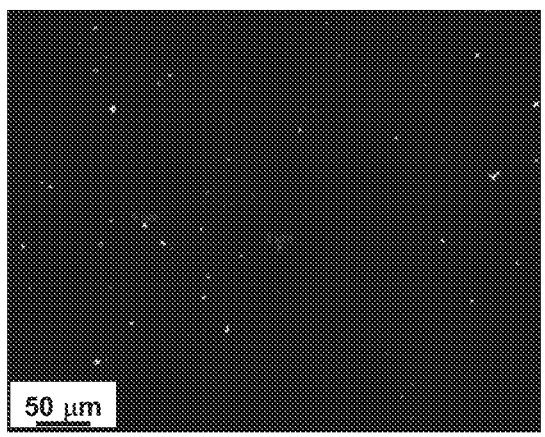
FIG. 2 is a depiction of fluorescence images of protease coating prepared via adsorption and covalent cross-linking.
Figure 2:
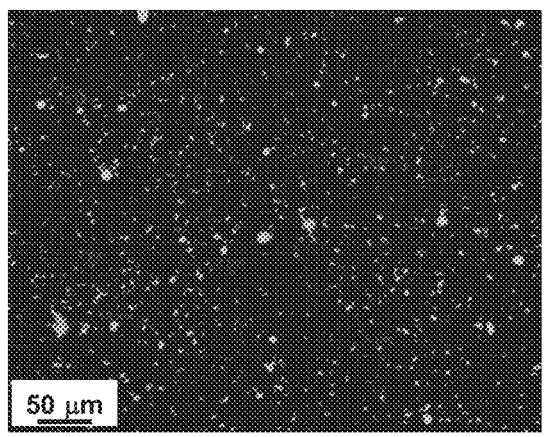

Fluorescent dye (Oregon green, Invitrogen Corp.) was first dissolved in dimethyl sulfoxide at a concentration of 2 mg/ml. The sample plates with physically adsorbed and covalently immobilized enzyme were incubated in the dye solution at room temperature with gentle shaking for 2 hours, followed by rinsing with DI water. The plates were then dried in nitrogen and observed under a fluorescence microscope. The images are shown in FIG. 2, where green color denotes the area covered with enzyme. Compared with physical adsorption, much more enzyme was immobilized on the surface using covalent cross-linking method.

Example 5

Determination of Enzyme Loading

Figure 3:
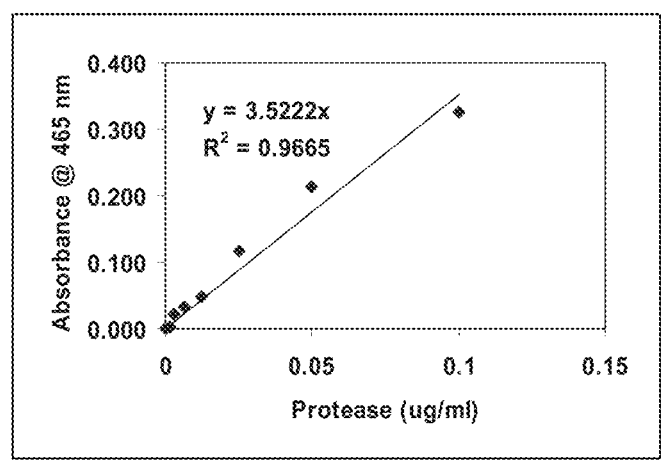
FIG. 3 shows a protein assay calibration curve.

The amount of enzyme attached to the plastic plate was determined by a reversed Bradford method. Typically, a working solution was first prepared by diluting Bradford reagent with DI water (1:5, by volume). A calibration curve was first obtained using free protease as the standards. In a 1 ml cuvette, 0.5 ml of protease solution was mixed with 0.5 ml of the working solution and then allowed to react for 5 min. The absorbance of the solution was measured at 465 nm on a spectrophotometer. After testing a series of different protease concentrations, a calibration curve was obtained as shown in FIG. 3.

To determine the loading of immobilized enzyme, a piece of enzyme-coated plate (1 cm×2 cm) was placed into a 20-ml glass vial, followed by the addition of 0.5 ml of DI water and 0.5 ml of the working solution. The vial was slightly agitated for 5 min at room temperature to allow binding of the dye to the immobilized enzyme. The absorbance of the supernatants was then recorded at 465 nm. Similarly a blank plastic plate without enzyme coating was also measured as the control. The reading obtained with the blank plate was subtracted from the reading obtained from the enzyme loaded plate. Comparing the obtained reading difference with the calibration curve gave the loading on the plate, which was then normalized into a unit of µg/cm². The enzyme loading by covalent cross-linking and physical adsorption were 8.5 and 1.0 µg/cm², respectively.

Example 6

Verification of the Proteolytic Activity of Enzyme Coating

Enzyme in solution: The proteolytic activity of protease was determined using 0.65% (w/v) casein as the substrate. Protease solution (0.1 ml) was incubated with 0.5 ml of casein solution for 10 min at 37° C. The reaction was stopped by the addition of 0.5 ml of tricholoroacetic acid (110 mM). The mixture was centrifuged to remove the precipitation. The resulting supernatant (0.4 ml) was mixed with 1 ml of sodium carbonate (0.5 M) and 0.2 ml of diluted Folin & Ciocalteu's phenol reagent (1:4 by diluting Folin & Ciocalteu's phenol reagent with DI water), followed by incubation at 37° C. for 30 min. Finally the mixture was centrifuged again and the absorbance of the supernatant was measured at 660 nm on a spectrophotometer. Blank experiment was performed without enzyme solution by adding 100 µl of buffer and carrying out similar test. The absorbance of the blank was subtracted from the sample (enzyme solution).

Figure 4:
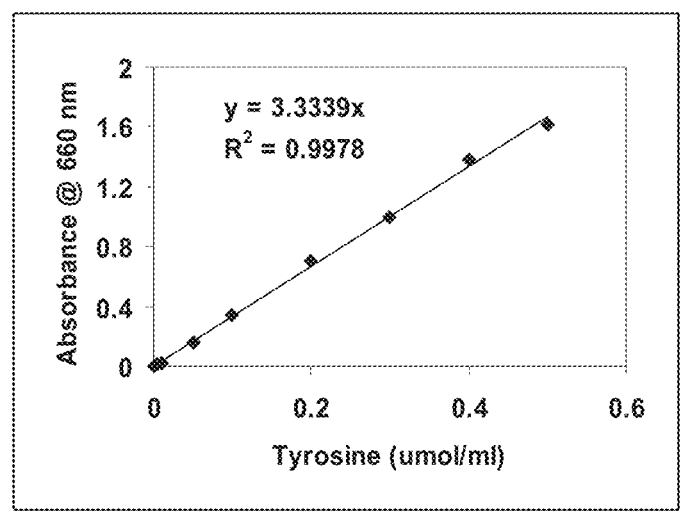
FIG. 4 shows a calibration curve for tyrosine (product of hydrolysis).

The activity unit was defined as: one unit of enzyme hydrolyzes casein to produce absorbance difference equivalent to 1.0 µmol of tyrosine per minute at 37° C. under the conditions of the assay. Tyrosine amino acid was used for calibration. Various concentrations of tyrosine were reacted with Folin-Ciocalteau reagent and the resulting calibration curve is shown in FIG. 4.

Enzyme coating: The activity of the immobilized protease was determined in a similar manner by using an enzyme coated polymer piece (1×2 cm) instead of enzyme in solution and a blank polymer coated piece as control. The activity of protein was termed as surface activity per unit area.

Results of activity assay showed that plates with covalent cross-linked protease afford $5.6 \times 10^{-3}$ unit/cm², while physical adsorbed enzyme only displayed an activity of $0.6 \times 10^{-3}$ unit/cm².

Example 7

Stain Degradation on Enzyme Coating

Figure 5:
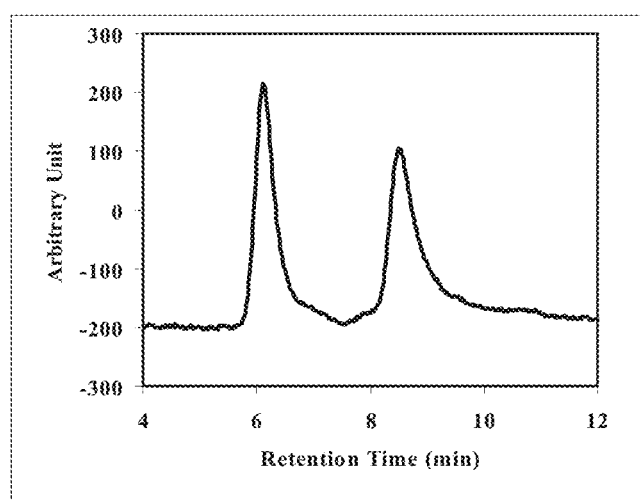
FIG. 5 shows a representative GPC chromatograph indicating egg white stain degradation.
Figure 6:
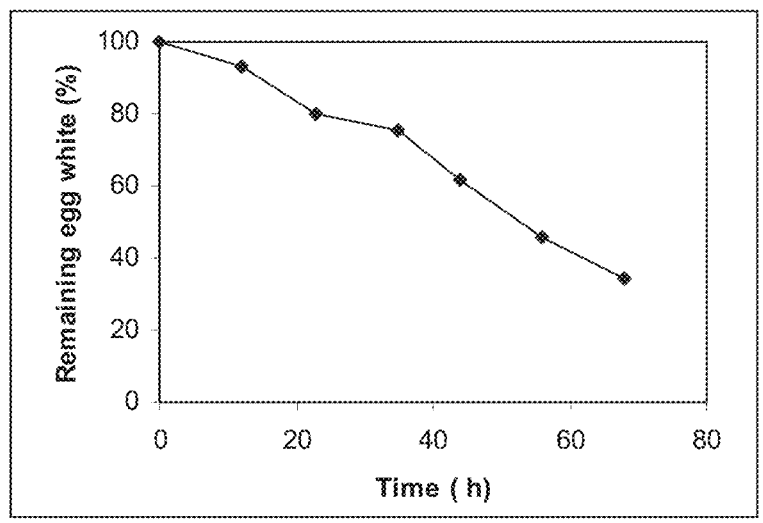
FIG. 6 shows the time course of egg white stain degradation.
Figure 7:
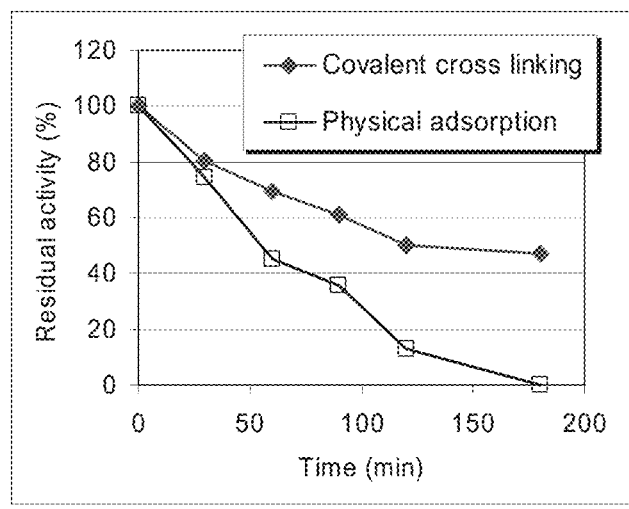
FIG. 7 shows thermal stability of protease coating at 80° C.

Egg white was used as the model stain to determine the stain degradation on enzyme coating. Onto a plate (11 cm in diameter) with protease-coating, 2 ml of egg white solution (10 mg/ml in DI water) was spin-coated at 2000 rpm. The plate was then cut into smaller pieces (1×2 cm) and kept at room temperature (25° C.) for various period of time to allow the degradation of egg white. After certain intervals, one small plate was carefully washed with DI water and the egg white in the washing solution was analyzed using gel permeation chromatography (GPC) to determine the molecular weight changes. Typically two peaks were found in the GPC chromatograph (FIG. 5): one has shorter retention time and the other has longer retention time, corresponding to the egg white and degradation products, respectively. Based on the area of the egg white peaks, a time course of egg white degradation was obtained as shown in FIG. 6. Control experiments were also performed using plates without protease coating, but no clear product peaks were identified.

Example 8

Thermal Stability of the Enzyme Coating

Thermal stability of the enzyme coating was studied at 80° C. in an air-heating oven. At certain time intervals, the sample plate(s) were taken out of the oven and the activity were measured following the procedure as described in Working Example 2. The decrease of activity with time was plotted in FIG. 9. It appeared that covalent cross-linked enzyme afforded better stability against thermal inactivation, as compared to physical adsorbed enzyme.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified or synthesized by one of ordinary skill in the art without undue experimentation.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A composition for removing stains from a solid surface comprising:
   a digestive protein capable of decomposing stain forming molecules;
   a substrate applied to the solid surface; and
   a linker moiety bound to an outer surface of said substrate and an active group of said digestive protein, said linker moiety between said protein and said substrate and covalently linking said protein to a surface of said substrate by an amide bond, the linker moiety between a free amine of said protein and said outer surface of said substrate;
   said digestive protein forming a layer on a surface of said substrate such that the digestive protein is surface exposed for reaction with a stain.

2. The composition according to claim 1, wherein the digestive protein comprises a lysozyme, protease, lipase, cellulase, glycosidase, or amylase.

3. The composition according to claim 1 wherein said free amine is in a lysine, arginine, asparagine, glutamine, or an N-terminal end.

4. The composition according to claim 1, wherein the digestive protein comprises a lipase.

5. The composition according to claim 1, wherein said substrate comprises paint or polymers.

\* \* \* \* \*